(12) United States Patent
Iyer et al.

(10) Patent No.: US 11,636,262 B2
(45) Date of Patent: Apr. 25, 2023

(54) METHOD AND SYSTEM FOR PROVIDING USER-SPECIFIC EXPLANATIONS FOR OUTPUT GENERATED BY ARTIFICIAL NEURAL NETWORK MODEL

(71) Applicant: Wipro Limited, Bangalore (IN)

(72) Inventors: Manjunath Ramachandra Iyer, Bangalore (IN); Chandrashekar Bangalore Nagaraj, Bangalore (IN)

(73) Assignee: Wipro Limited, Bangalore (IN)

( * ) Notice: Subject to any disclaimer, the term of this patent is extended or adjusted under 35 U.S.C. 154(b) by 690 days.

(21) Appl. No.: 16/741,992

(22) Filed: Jan. 14, 2020

(65) Prior Publication Data

US 2021/0165954 A1 Jun. 3, 2021

(30) Foreign Application Priority Data

Nov. 29, 2019 (IN) .............................. 201941049107

(51) Int. Cl.
*G06F 40/242* (2020.01)
*G06F 40/56* (2020.01)
*G16H 70/00* (2018.01)

(52) U.S. Cl.
CPC ............ *G06F 40/242* (2020.01); *G06F 40/56* (2020.01); *G16H 70/00* (2018.01)

(58) Field of Classification Search
None
See application file for complete search history.

(56) References Cited

U.S. PATENT DOCUMENTS

| | | | |
|---|---|---|---|
| 2018/0322406 A1* | 11/2018 | Merrill | G06N 20/00 |
| 2019/0318261 A1* | 10/2019 | Deng | G06K 9/6256 |
| 2019/0354805 A1* | 11/2019 | Hind | G06V 10/764 |
| 2020/0250556 A1* | 8/2020 | Nourian | G06Q 10/0635 |
| 2020/0311798 A1* | 10/2020 | Forsyth | G06F 40/30 |
| 2021/0133642 A1* | 5/2021 | Yuan | G06F 9/542 |
| 2022/0284579 A1* | 9/2022 | Nye | G16H 40/63 |

OTHER PUBLICATIONS

Fernando, I., et al., "A Domain Specific Expert System Model for Diagnostic Consultation in Psychiatry", 2011 12th ACIS International Conference on Software Engineering, Artificial Intelligence, Networking and Parallel/Distributed Computing, pp. 3-6.

(Continued)

*Primary Examiner* — Ariel Mercado
(74) *Attorney, Agent, or Firm* — Finnegan, Henderson, Farabow, Garrett & Dunner, LLP

(57) ABSTRACT

This disclosure relates to method and system for providing user-specific explanations for an output generated by an Artificial Neural Network (ANN) model. The method may include receiving a training dataset, and identifying one or more relevant features from the training dataset. The method may further include distributing the one or more relevant features into a plurality of groups. The plurality of groups may correspond to a plurality of levels of domain knowledge of users. The method may further include generating a plurality of vocabularies of explanations for an output generated by the ANN model for the training dataset corresponding to the plurality of groups, using the one or more relevant features.

17 Claims, 10 Drawing Sheets

(56) References Cited

OTHER PUBLICATIONS

Hind, M. et al., "TED: Teaching AI to Explain its Decisions", AIES '19, Jan. 27-28, 2019, pp. 123-129.
Ribera, M., et al., "Can we do better explanations? A proposal of User-Centered Explainable AI", 2019 CEUR-WS.org/Vol-2327/IUI19WS-ExSS2019-12.pdf, 7 pages.
Bai, S., et al., "A Survey on Automatic Image Caption Generation", May 2018, Neurocomputing, (17 pages).

* cited by examiner

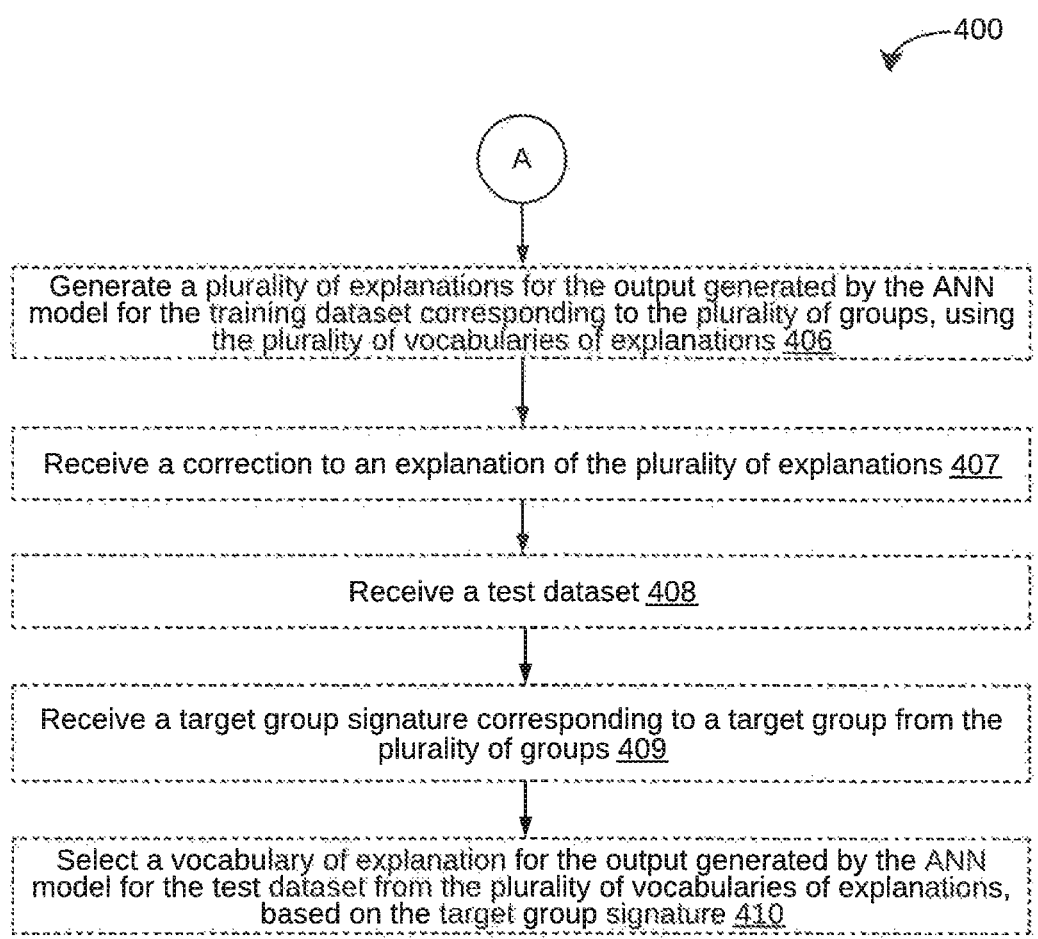
FIG. 4 contd.

| Entity | Entity type | Image/video segment | Maximum active neurons of each layer |
|---|---|---|---|
| Ball | Object | Ball1.jpg | L1->(3,4)(2,3) L2-> ... |
| Hitting ball with a bat | interaction | Hit1.jpg | ... |
| Ball moving to goal | action | Ball_move1.mp4 | ... |
| Big red ball | attribute | Ball1.txt | ... |

601 — Entity
602 — Entity type
603 — Image/video segment
604 — Maximum active neurons of each layer
600

FIG. 6

METHOD AND SYSTEM FOR PROVIDING USER-SPECIFIC EXPLANATIONS FOR OUTPUT GENERATED BY ARTIFICIAL NEURAL NETWORK MODEL

TECHNICAL FIELD

This disclosure relates generally to artificial neural network (ANN), and more particularly to method and system for providing user-specific explanations for an output generated by an ANN.

BACKGROUND

Artificial Intelligence (AI) models work as black boxes which provide little or no insights about how a decision was generated by the AI model. As it will be appreciated by those skilled in the art, an explanation or a resoning on "Why a certain decision is made?" would be very useful for an end user. For example, during diagnosis of cancer from a plurality of Computed Tomography (CT) images, it would be helpful if a classifier model (e.g. an AI model) provides information to the user about generated decision in simple and plain English about. "What features were taken into consideration to generate the decision". Further, such information would be convincing for the user, as the same can be referred back to the CT images for validation.

The explanations generated by the AI models have become increasingly popular. Moreover, providing explanations is seen as a regulatory obligation, in order to make the decision making process by the AI models more transparent. The explainable AI models are trained based on different type of users in the same domain. In an example scenario, the explainable AI model may be trained using data associated with a set of doctors having different specializations. Further, the explainable AI models may be trained based on the users corresponding to different domains. In another example scenario, the explainable AI models may be trained using data associated with doctors, domain experts, and non-domain experts. In such a scenario, the explanations generated are same for all the users, irrespective of the type of users. These kind of explanations may not be helpful and comprehendible for all the users. In other words, the explanations generated by these conventional AI models may not consider the domain of the user or his/her expertise in understanding and comprehending the technical jargons used in the generated explanation. For example, if the generated explanations are technical and filled with domain specific words, layman users may not be able to understand the explanations, although the domain experts may easily decode the generated explanations. On the other hand, explanations which are too general in nature (so as to satisfy a wide range of users) may create confusion and may not be able to provide required details to a specific class of users to take an improved decision.

Explainable AI models, for example, explainable image classification models, may provide explanations, heat map, and visualization of the AI model for an input image. Further, these AI models may generate explanations which provide a reasoning about "why the input image was classified to a particular class". However, these generated explanations may be difficult to understand by the non-domain users. As a result, the users may not use these AI models at all. For example, for a classifier model (AI model) trained for classifying pneumonia images, the explanations may be generated using a set of medical attributes, due to which a non-domain user (for example, a patient) may not be able to understand the explanation due to presence of complicated domain-specific words. Further, these explainable AI models may not be able to identify attributes from the images to build vocabulary (for a first time) to provide explanations. Moreover, these explainable AI models may not be able to identify different and matching attributes in the activations of neurons of the AI model so as to provide explanations for different classes of users. Further, these explainable AI models may not be able link wordings in the explanation to the activations of the neurons selected together with the category of the user.

SUMMARY

In one embodiment, a method of providing user-specific explanations for an output generated by an Artificial Neural Network (ANN) model is disclosed. The method may include receiving a training dataset, and identifying one or more relevant features from the training dataset. The method may further include distributing the one or more relevant features into a plurality of groups. The plurality of groups may correspond to a plurality of levels of domain knowledge of users. The method may further include generating a plurality of vocabularies of explanations for the output generated by the ANN model for the training dataset corresponding to the plurality of groups, using the one or more relevant features.

In one embodiment, a system for providing user-specific explanations for an output generated by an ANN model is disclosed. The system may include a vocabulary and explanation generating device, which may include at least one processor and a memory communicatively coupled to the at least one processor. The memory may store processor-executable instructions, which, on execution, may cause the processor to receive a training dataset, and identify one or more relevant features from the training dataset. The processor-executable instructions, on execution, may further cause the processor to distribute the one or more relevant features into a plurality of groups. The plurality of groups may correspond to a plurality of levels of domain knowledge of users. The processor-executable instructions, on execution, may further cause the processor to generate a plurality of vocabularies of explanations for an output generated by the ANN model for the training dataset corresponding to the plurality of groups, using the one or more relevant features.

In one embodiment, a non-transitory computer-readable medium storing computer-executable instructions for providing user-specific explanations for an output generated by an ANN model is disclosed. The stored instructions, when executed by a processor, may cause the processor to perform operations including receiving a training dataset, identifying one or more relevant features from the training dataset, distributing the one or more relevant features into a plurality of groups, wherein the plurality of groups correspond to a plurality of levels of domain knowledge of users, and generating a plurality of vocabularies of explanations for an output generated by the ANN model for the training dataset corresponding to the plurality of groups, using the one or more relevant features.

It is to be understood that both the foregoing general description and the following detailed description are exemplary and explanatory only and are not restrictive of the invention, as claimed.

BRIEF DESCRIPTION OF THE DRAWINGS

The accompanying drawings, which are incorporated in and constitute a part of this disclosure, illustrate exemplary embodiments and, together with the description, serve to explain the disclosed principles.

FIG. 6 is a Table of objects and actions detected in an image and the corresponding explanations, in accordance with some embodiments of the present disclosure.

DETAILED DESCRIPTION

Exemplary embodiments are described with reference to the accompanying drawings. Wherever convenient, the same reference numbers are used throughout the drawings to refer to the same or like parts. While examples and features of disclosed principles are described herein, modifications, adaptations, and other implementations are possible without departing from the spirit and scope of the disclosed embodiments. It is intended that the following detailed description be considered as exemplary only, with the true scope and spirit being indicated by the following claims.

Figure 1:
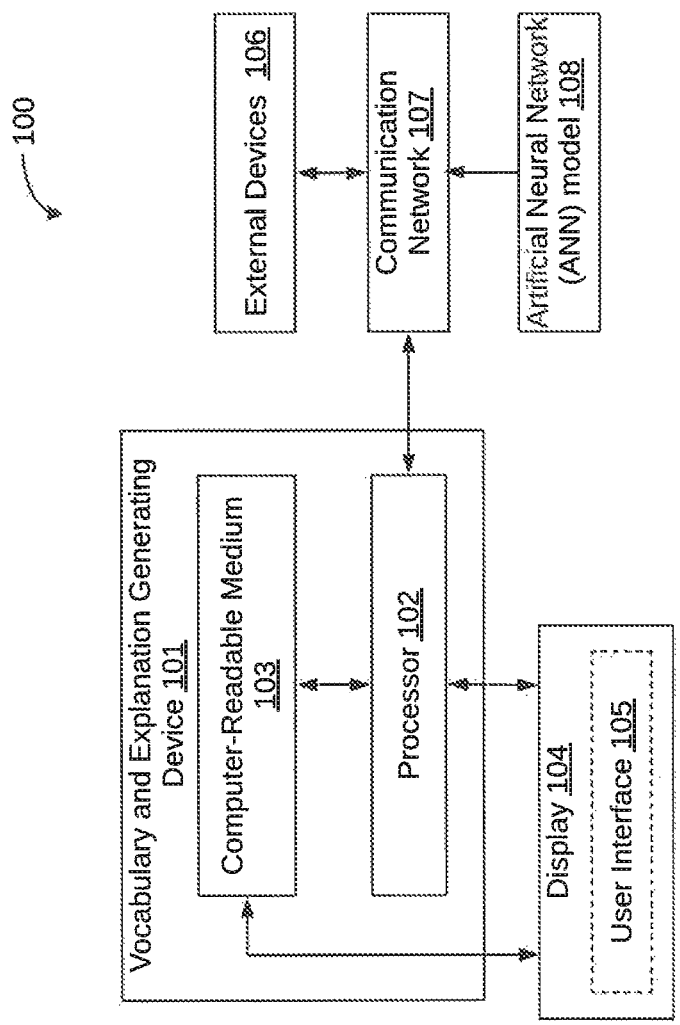
FIG. 1 is a block diagram of an exemplary system for providing user-specific explanations for an output generated by an Artificial Neural Network (ANN) model, in accordance with some embodiments of the present disclosure.

Referring now to FIG. 1, an exemplary system 100 for providing user-specific explanations for an output generated by an ANN model is illustrated, in accordance with some embodiments of the present disclosure. As will be appreciated, the system 100 may implement the ANN model for a target classification application. Further, the system may implement an ANN engine in order to provide user-specific explanations for an output generated by the ANN model. In particular, the system 100 may include a vocabulary and explanation generating device 101 (for example, server, desktop, laptop, notebook, netbook, tablet, smartphone, mobile phone, or any other computing device) that may implement the ANN engine. It should be noted that, in some embodiments, the ANN engine, by providing user-specific explanations for an output generated by an ANN model, may help in understanding the reason for the decisions taken by the ANN and, therefore, improve the classifications performed by the ANN model.

As will be described in greater detail in conjunction with FIGS. 2-9, the vocabulary and explanation generating device may receive a training dataset. The vocabulary and explanation generating device may further identify one or more relevant features from the training dataset. The vocabulary and explanation generating device may further distribute the one or more relevant features into a plurality of groups. It may be noted that the plurality of groups may correspond to a plurality of levels of domain knowledge of users. The vocabulary and explanation generating device may further generate a plurality of vocabularies of explanations for an output generated by the ANN model for the training dataset corresponding to the plurality of groups, using the one or more relevant features.

The system 100 may include a vocabulary and explanation generating device 101. In some embodiments, the vocabulary and explanation generating device 101 may include one or more processors 102 and a computer-readable medium (for example, a memory) 103. The system 100 may further include a display 104. The system 100 may further include an ANN model 108 which may generate an output (e.g. a classification) for an input data. The computer-readable storage medium 103 may store instructions that, when executed by the one or more processors 102, cause the one or more processors 102 to provide user-specific explanations for the output generated by the ANN model 108, in accordance with aspects of the present disclosure. The computer-readable storage medium 103 may also store various data (for example, relevant feature data, group data, group signature, captions data, correction to explanation data, hierarchical graph, feature table, activated neuron data, and the like) that may be captured, processed, and/or required by the system 100. The system 100 may interact with a user via a user interface 105 accessible via the display 104. The system 100 may also interact with one or more external devices 106 over a communication network 107 for sending or receiving various data. The external devices 106 may include, but may not be limited to, a remote server, a digital device, or another computing system.

Figure 2:
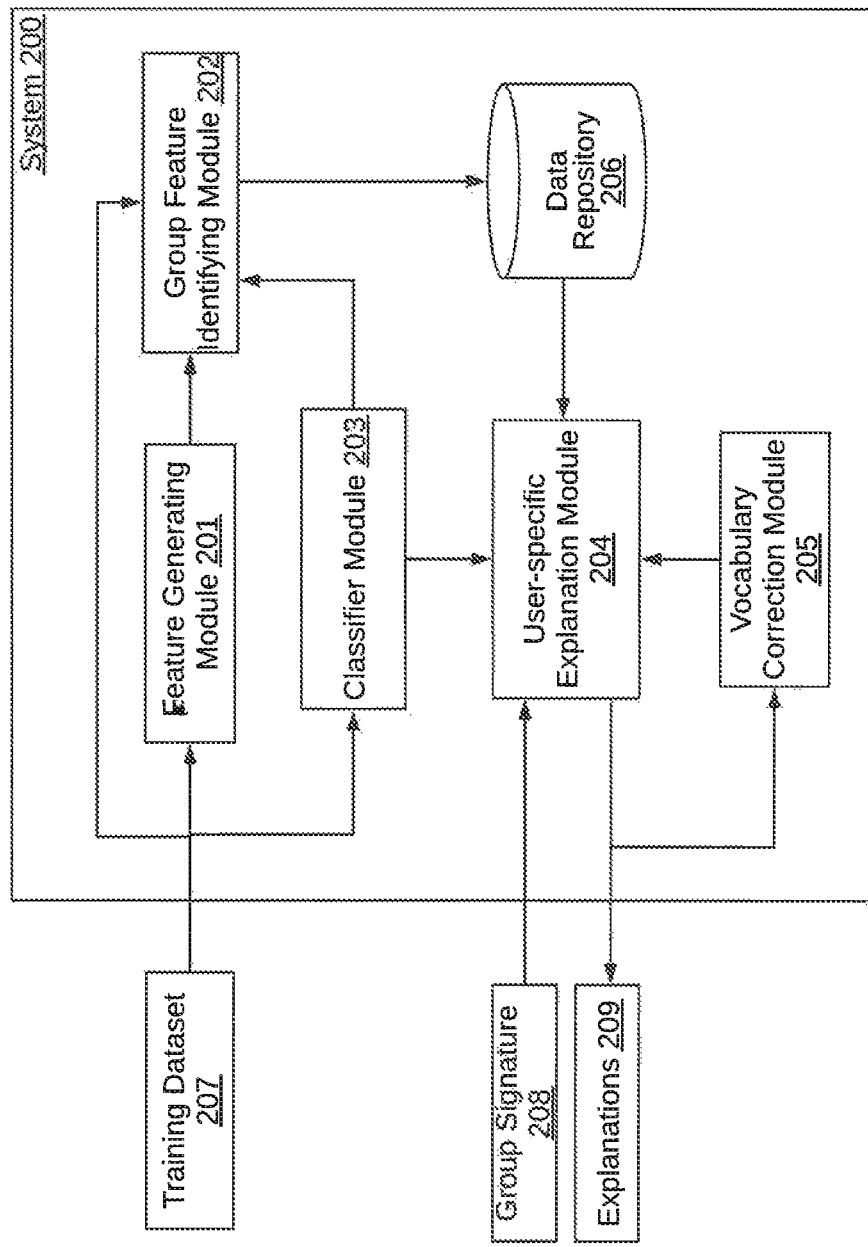
FIG. 2 is a functional block diagram of a system for providing user-specific explanations for an output generated by an ANN model, in accordance with some embodiments of the present disclosure.

Referring now to FIG. 2, a functional block diagram of a system 200 for providing user-specific explanations for an output generated by an ANN model, is illustrated, in accordance with some embodiments of the present disclosure. The system 200 may include a feature generating module 201, a group feature identifying module 202, a classifier module 203, a user-specific explanation module 204, a vocabulary correction module 205, and a data repository 206.

The feature generating module 201 may receive training dataset 207. In some embodiments, the training dataset 207 may include an image which may be used for training the user-specific explanation module 204. In some embodiments, the image may be cropped to 28>28 and provided as input to the feature generating module 201 for extracting the features and associated objects. The image may be provided as input to the group feature identifying module 202 and the classifier module 203 for generating image signatures. It may be noted that the classifier module 203 may also provide the class information (output) of the image.

After receiving the training dataset 207, the feature generating module 201 may extract one or more features from the training dataset (i.e. all the images used in a classifier model). In some embodiments, the one or more features may include different objects in the image (i.e. training dataset), their interactions, actions, and attributes. For example, the attributes may include a color, a shape, a size, a position, an interaction with other objects and surroundings, and a form the object can take (for example, for a blocked coronary artery (object), an attribute may include a percentage of blockage).

In some embodiments, a vocabulary of explanations may be derived by parsing one or more captions associated with the image, or by using words which are provided by a domain expert. It may be noted that the captions may be generated based on the objects and their interactions in the scene. By way of another example, the feature generating module 201 may further include a caption generator (not shown in FIG. 2). The caption generator (not shown in FIG. 2) may be trained with different objects and their interactions. For example, conventional caption generators, such as Common Objects in Context (COCO) may be used to generate the one or more captions. In some embodiments, the feature generating module 201 may include a Natural Language Processing (NLP) engine which may generate the attributes. Once the captions are generated, the captions may be fed to the NLP engine which may extract at least one of named entities, verbs, adverbs, and adjectives. It may be noted that this extracted information may form the attributes of the objects.

The group feature identifying module 202 may receive the training dataset (image) 207. It may be understood that the training dataset 207 may indicate the type of images which may be used as input. The group feature identifying module 202 may not perform any processing on the received image. The group feature identifying module 202 may identify commonly encountered objects in the received image. The group feature identifying module 202 may identify common objects in the image at varying levels of abstraction. Further, the group feature identifying module 202 may be configured to receive the features and attributes from the feature generating module 201, and segregate the attributes that are specific to a group.

As it will be appreciated by those skilled in the art, a different explanation for the output (from the classifier module 203) may be provided to different user groups, based on a level of expertise of users of each user group, a familiarity of the vocabulary, and usage of the explanation. In some embodiments, a hierarchy of attributes may be formed. For example, for a coronary angio image, the hierarchy of attributes may be as shown below:

Heart>blood vessels and chambers>blocked blood vessels

The hierarchy of attributes may map to hierarchy of expertise of the users (of different user groups). In some embodiments, the hierarchy of expertise of the users may be specified at the time of training. For example, a hierarchy of expertise of the users may be as shown below:

Patient>medical attendant>Radiologist

It may be noted that different user groups may be organized hierarchically into multiple levels, based on domain knowledge which the respective users need to comprehend and use the explanation. The attributes may be mapped to these multiple levels. The hierarchy of attributes may be mapped to the different users at the time of training, by a domain expert. The users may be provided with password or group signatures 208. The group signatures 208 may eventually map to the different levels of hierarchy of the attributes. In some embodiments, sample records of the explanation for each group may be used. In alternate embodiment, the mapping may be performed heuristically (i.e. the levels may be mapped to hierarchy of attributes). It may be noted that the system may learn the vocabularies of explanations (corresponding to different user groups) and attributes with the right mapping adaptively in the vocabulary correction module 205. In some embodiment, the different groups may have one or more attributes in common. In some embodiments, the group feature identifying module 202 may generate a feature table including the attributes. The group feature identifying module 202 may send the feature table to the data repository 206 for storing the same.

The data repository 206 may receive the feature table from the group feature identifying module 202. In some embodiments, the data repository 206 may be a fast-accessible storage that may store intermediate results. The data repository 206 may be accessed by the user-specific explanation module 204 for referring back to the attributes. It may be noted that the feature table may be made available for the user-specific explanation model 204 for decision-making.

The classifier module 203 may receive the training dataset (image) 207. After receiving the training dataset 207, the classifier module 203 may generate image signatures. In some embodiments, the classifier module 203 may use a Convolutional Neural Network (CNN) for generating the image signatures. In alternate embodiments, the classifier module 203 may use auto-encoders for generating the image signatures.

The user-specific explanation module 204 may be configured to receive the feature table from the data repository 206 and the image signatures from the classifier module 203. The user-specific explanation module 204 may be configured to receive the group signature 208. It may be noted that the group signature 208 may indicate a type of user for which the explanations need to be generated at multiple hierarchical levels. In some embodiments, the user may provide the group signatures 208.

In some embodiments, the user-specific explanation module 204 may receive the features of the image at the output of a penultimate layer of the ANN model (for example, the CNN based classifier module 203), concatenated with the group signatures (for example, a password) 208. For the purpose of training, the training dataset 207 and their corresponding attributes (for example, a class of the classifier module and group of the user) may be received from the data repository 206.

Then the user-specific explanation module 204 may generate explanations 209 from the attributes using a Long Short Term Memory (LSTM) model. The explanations 209 may be generated word by word. It may be further noted that the next word of the sequence may be generated based on the concatenated data and the current word generated by the system. The LSTM model may generate probabilities for different words in the vocabulary to be the next word. A word with the highest probability is selected as the next word. Based on the group signatures 208, distinct explanations may be generated for each of the training image. In other words, multiple explanations for an output generated by the ANN model may be generated for each image corresponding to the different user groups.

The vocabulary correction module 205 may receive the generated explanations 209 from the user-specific explanation module 204, and may help in fine-tuning the explanations 209. In another embodiment, the vocabulary correction module 205 may help in obtaining right activation (i.e. signatures) as an input to the user-specific explanation module 204. Further, the vocabulary correction module 205 may receive the corrections to be made to the explanations 209 from the user through a User Interface (UI) based on if the word is from the correct vocabulary specific to the class or if it is from the vocabulary of other class. It may be noted that even in the case a word is identified in the right class, the word should be from the vocabulary maintained for the right class of the user. The vocabulary correction module 205 may send the fine-tuning parameters to the user-specific explanation module 204. The vocabulary correction module 205 may capture any outlandish vocabulary for a user-group and may eliminate the same in subsequent explanations.

Figure 3:
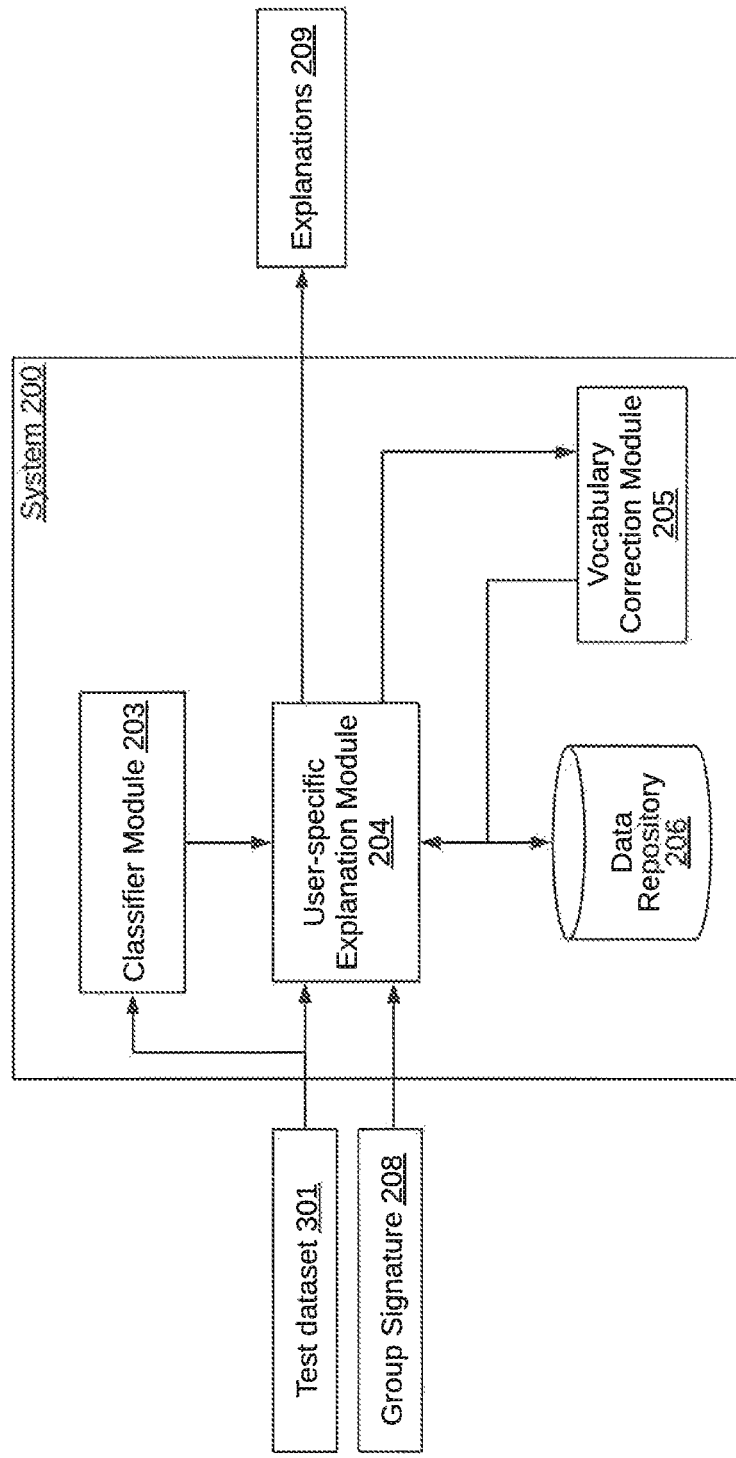
FIG. 3 is a functional block diagram of a system for providing user-specific explanations for an output generated by an ANN model, in accordance with some alternate embodiments of the present disclosure.

Referring now to FIG. 3, a functional block diagram of a system 200 for providing user-specific explanations for an output generated by an ANN model during test phase (using test dataset), is illustrated, in accordance with some embodiments of the present disclosure. The system 200 may include the classifier module 203, the user-specific explanation module 204, the vocabulary correction module 205, and the data repository 206.

In some embodiments, the classifier module 203 may receive a test dataset 301. In some embodiments, test dataset 301 may be an image file or a video file. Upon receiving the test dataset 301, the classifier module 203 may generate image signatures or password. The test dataset 301 may be typically a 28×28 size image or cropped to that size. It may be understood that the system 200 may generate user-specific explanations 209 for an output generated for the test dataset 301 by the classifier module 203. It may be further understood that the generated explanations 209 may indicate the class to which the image belongs in addition to the reason for classifying the image into that specific class.

The user-specific explanation module 204 may receive the test dataset 301. The user-specific explanation module 204 may further receive image signature from the classifier module 203. Furthermore, the user-specific explanation module 204 may receive group signature (i.e. group identity) 208 from a user. It may be noted that the group signature 208 may indicate a user group for which the explanation is sought. In some embodiments, the group signature 208 may be provided to the user in the form of password or login credential that identify the user group.

The user-specific explanation module 204 may further receive the feature table (also called attribute table) from the data repository 206. The user-specific explanation module 204 may be configured to generate explanations 209 for the classification of the test dataset 301. Further, user-specific explanation module 204 may receive image signature and user-group identity for which a customized explanation is to be generated.

In some embodiments, the data repository 206 may store connecting words of the language, such as prepositions, articles, conjunctions, etc., which may provide vocabulary to be used while generating the explanations for a user-group. The vocabulary may be stored as look-up table for the probability of next word generated by the LSTM in the user-specific explanation module 204. It may be noted that the image features tapped from the penultimate layer of the classifier module 203 may bind to the vocabulary specific to the group through the LSTM model to generate human readable sentences.

The user-specific explanation module 204 may further receive the features of the image being classified and concatenated with the required signature (thereby, identifying a class of the user). The user-specific explanation module 204 may include a LSTM module which may be configured to generate the explanation in the form of text in real-time.

The data repository 206 may store the vocabulary and feature table specific to the indicated group of the user. In some embodiments, the data repository 206 may include a radius server.

The vocabulary correction module 205 may receive the explanations 209 from the user-specific explanation module 204. In some embodiments, the vocabulary correction module 205 may help in updating the vocabulary specific to group of users and for a specific class of the classifier output, so as to support adaptive and continuous learning from the user input. It may be noted that the vocabulary binding with different image features may be fine-tuned by the vocabulary correction module 205, especially, during the training phase.

Figure 4:
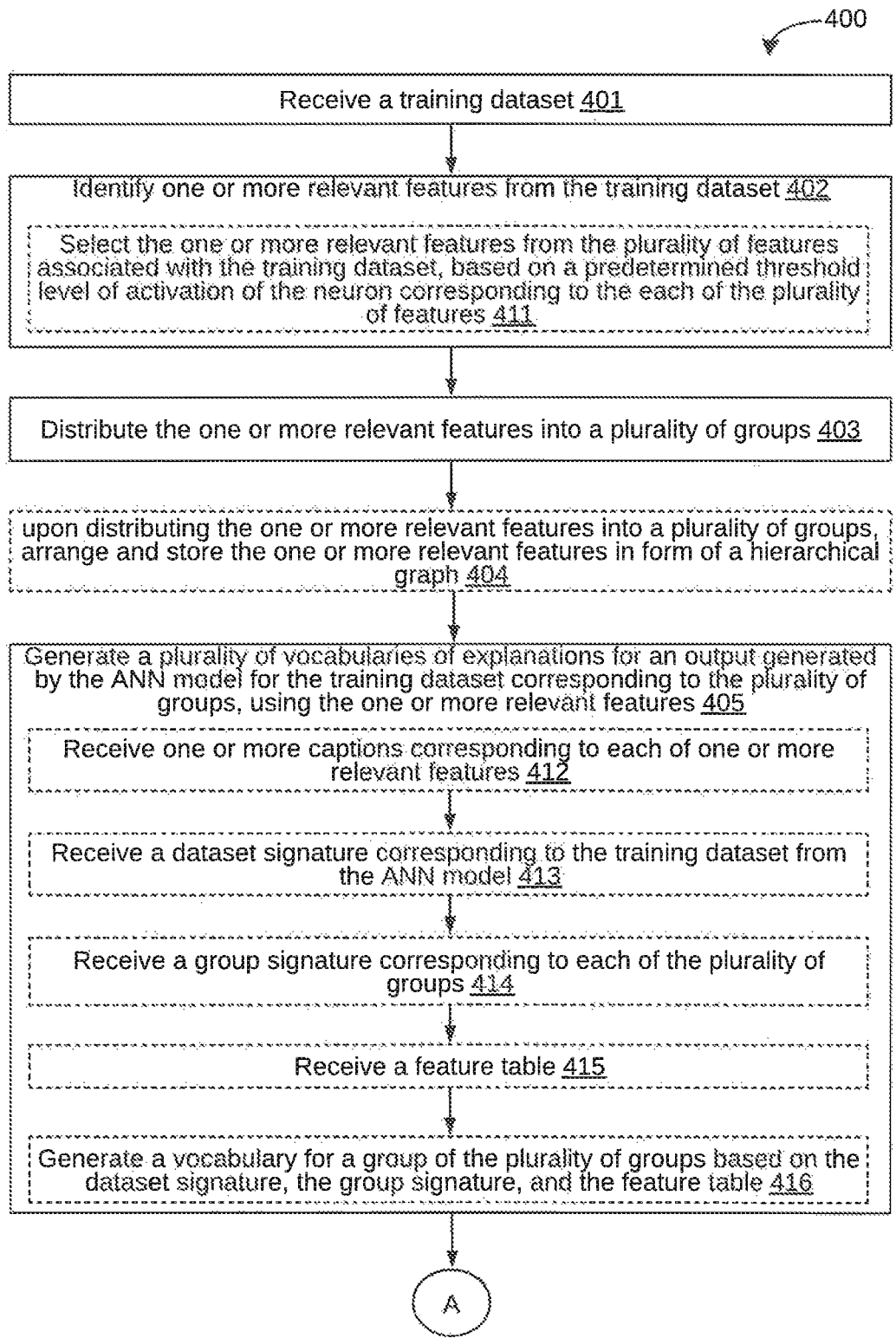
FIG. 4 is a flow diagram of an exemplary process for providing user-specific explanations for an output generated by an ANN model, in accordance with some embodiments of the present disclosure.

Referring now to FIG. 4, an exemplary control logic 400 for providing user-specific explanations for an output generated by an ANN model is depicted via a flowchart, in accordance with some embodiments of the present disclosure.

At step 401, a training dataset 207 may be received. In some embodiments, the training dataset 207 may include an image file or a video file. At step 402 one or more relevant features may be identified from the training dataset 207. In some embodiments, the identifying may further include a step 411. It may be noted that the one or more relevant features may include at least one of one or more objects within the training dataset 207, an interaction between two or more objects within the training dataset 207, an action associated with an object, or one or more attributes associated with each of the one or more objects, wherein the one or more attributes comprise at least one of a color of the object, a shape of the object, a size of the object, a position of the object, or an interaction of the object with other objects and surroundings. In some embodiments, the one or more relevant features may be identified from a plurality of features associated with the training dataset 207. Further, each of the plurality of features may correspond to a neuron activated in the ANN model for generating an output for the training dataset 207.

At step 411, one or more relevant features may be selected from the plurality of features associated with the training dataset 207, based on a predetermined threshold level of activation of the neuron corresponding to the each of the plurality of features. At step 403, the one or more relevant features may be distributed into a plurality of groups. It may be noted that the plurality of groups may correspond to a plurality of levels of domain knowledge of users.

In some embodiments, the control logic 400 may include an additional step of 404 at which, upon distributing the one or more relevant features into a plurality of groups, the one or more relevant features may be arranged and stored in form of a hierarchical graph. The hierarchical graph may represent the plurality of levels of domain knowledge of the users.

At step 405, a plurality of vocabularies of explanations may be generated for an output generated by the ANN model for the training dataset 207 corresponding to the plurality of groups, using the one or more relevant features. In some embodiments, generating the plurality of vocabularies of explanations may further include steps 412-416. For example, at step 412, one or more captions corresponding to each of the one or more relevant features may be received. It may be noted that the one or more captions may be generated using Common Objects in Context (COCO). It may be further noted that one or more attributes associated with each of the one or more relevant features may be generated from the one or more captions using Natural Language Processing (NLP). At step 413, a dataset signature corresponding to the training dataset 207 may be received from the ANN model. At step 414, a group signature 208 corresponding to each of the plurality of groups may be received. At step 415, a feature table may be received. The feature table may include connecting words of a language. At step 416, a vocabulary may be generated for a group of the plurality of groups based on the dataset signature, the group signature 208, and the feature table. In some embodiments, generating the plurality of vocabularies may further include feeding the one or more relevant features of the training dataset 207 at an output of a penultimate layer of the ANN model.

At step 406, a plurality of explanations may be generated for the output generated by the ANN model for the training dataset 207 corresponding to the plurality of groups, using the plurality of vocabularies of explanations. The plurality of explanations may be generated from the plurality of vocabularies of explanations using LSTM model.

At step 407, a correction to an explanation 209 of the plurality of explanations may be received from a user. In some embodiments, the correction to the explanation 209 may be based on determining by the user that a word in the explanation 209 corresponding to a group of the plurality of groups is from a vocabulary of explanation corresponding to the group. In alternate embodiments, the correction to the explanation 209 may be based on determining by the user that a word in the explanation 209 corresponding to a group is from a correct vocabulary of explanation 209 corresponding to the group.

It may be understood that the above steps may be performed during training of the system for providing user-specific explanations for an output generated by an ANN model. Once the system is trained, the system may be used during test phase (for test dataset) for providing user-specific explanations for an output generated by an ANN model. Accordingly, at step 408, a test dataset 301 may be received. At step 409, a target group signature corresponding to a target group may be received from the plurality of groups. At step 410, a vocabulary of explanation for the output generated by the ANN model for the test dataset 301 may be selected from the plurality of vocabularies of explanations, based on the target group signature.

Figure 5:
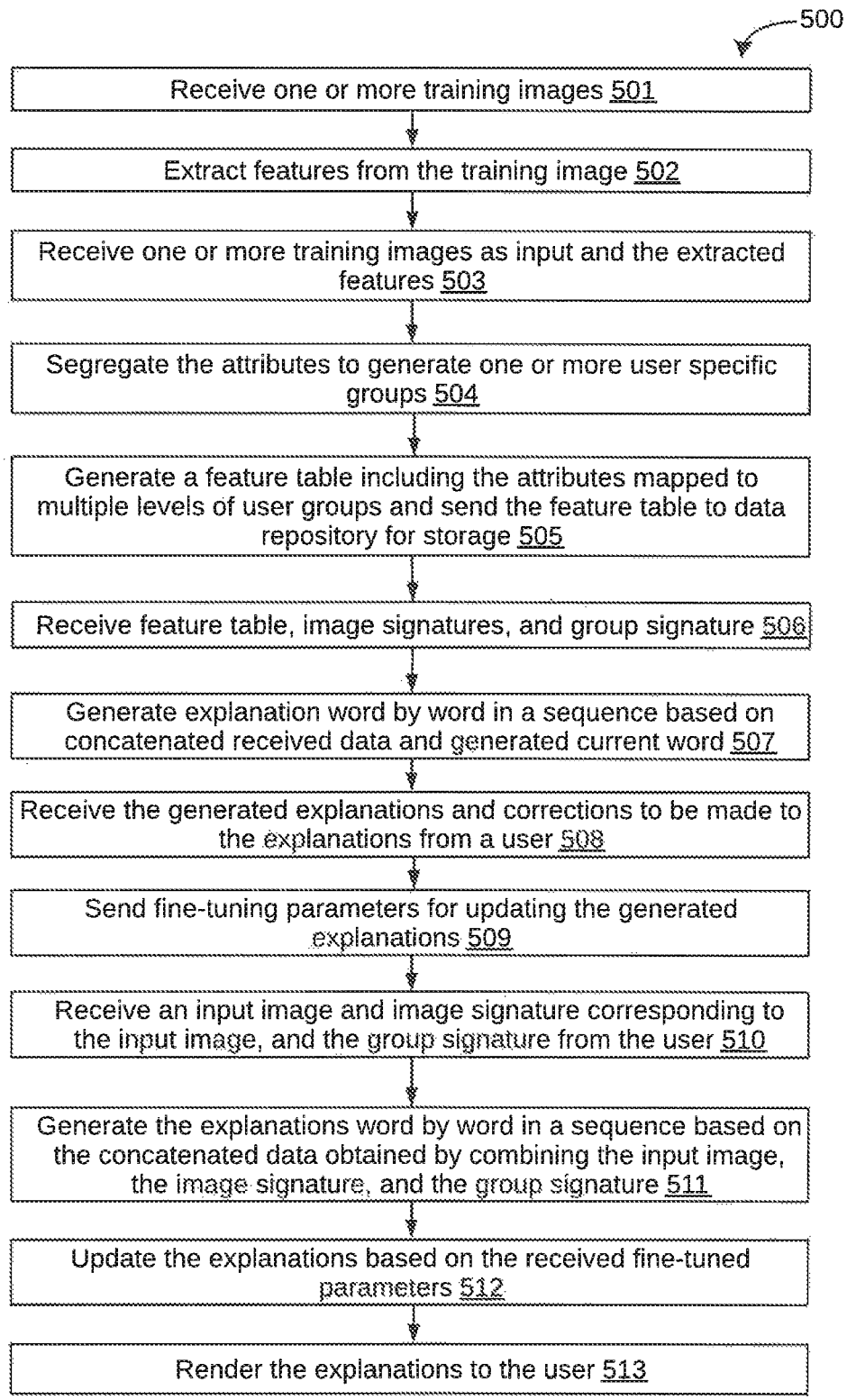
FIG. 5 is a flow diagram of a detailed exemplary process for providing user-specific explanations for an output generated by an ANN model, in accordance with some embodiments of the present disclosure.

Referring now to FIG. 5, an exemplary control logic 500 for providing user-specific explanations for an output generated by an ANN model is depicted in greater detail via a flowchart, in accordance with some embodiments of the present disclosure. Steps 501-510 of the control logic 500 may be performed in offline mode, or in other words, during training of the ANN model. Steps of 511-514 of the control logic 500 may be performed in online mode, or in other words, during testing of the ANN model. As illustrated in the flowchart, at step 501 one or more training images may be received from an image data repository. For example, the one or more training images may be received by the feature generating module 201. It may be understood that the one or more training images may be used for training the user-specific explanation module 204. In some embodiments, each of the one or more training images may be cropped to 28×28.

At step 502, one or more common features may be extracted from the training image. It may be noted that the one or more common features may include at least one of associated objects available in the image, interactions between the objects, actions performed by the objects, and attributes (descriptors) associated with each of the object. It may be further noted that the attributes (descriptors) may be used to generate vocabulary for explanations for an output generated by the ANN model.

In some embodiments, the feature generating module 201 may receive the training image (input image). After receiving the training images, the feature generating module 201 may extract the features from the training data 207 (i.e., all the training images used in the classifier module 203 development and corresponding explanations). It may be noted that the attributes may correspond to color, shape, size, position, interaction (with other objects), action, environment, forms it takes (for example, in a blocked coronary artery, the attributes may include a percentage of blockage).

In some embodiments, at step 502, additionally, features contributing for a desired explanation may be identified. These features contributing for the desired explanation may be identified based on the training dataset 207. The features identified in most of the training images of the training dataset 207 corresponding to a specific class may be included into the vocabulary for explanation. For example, features identified in a threshold minimum number of training images (e.g. a threshold of 90%) may be included into the vocabulary for explanation. In some embodiments, for identifying the features (for example, actions, interactions, objects, and the attributes), one or more conventional mechanisms including SURF, SIFT, HAAR feature and SVM, Random Forest, Decision Tree, and Neural Network may be used. For example, the feature generating module 201 may identify the features from each training image of the training dataset 207.

In some embodiments, maximum activation neurons in the ANN model (i.e. the classifier module 203) may be identified, for an output generated by the ANN model for an input image. By way of an example, all the neurons that are activated for an entity may be considered. In another example, only a fraction of neurons or a fixed number of neurons (for example, 6 neurons) may be considered. In some embodiments, activation level of the neurons may be arranged in a descending order, and neurons within 50% of the maximum activation may be considered. Further, the neurons of each layer may be identified and entered into a Table with row and column address. An exemplary Table is shown in FIG. 6.

Referring now to FIG. 6, a Table 600 of objects and actions detected in an image and the corresponding explanations is illustrated, in accordance with an embodiment. In the Table 600, column 601 includes entities in the image, column 602 includes entity types of the respective entities, column 603 includes image segments (or video segment) of the image which shows the respective entities, and column 604 includes the maximum neurons which are active in each layer, for the respective entities. For example, as shown in the FIG. 6, the entities listed in the column 601 may include a 'ball', a 'hitting ball with a bat', a 'ball moving to goal', and a 'big red ball', and entity types (of the entities of Column 601) listed in the Column 602 may include an 'object', an 'interaction', an 'action', and an 'attribute'. For example, for the entity 'ball' of the entity type 'object' in an image segment 'Ball1_jpg' of an image, neuron (3,4) and (2,3) of layer L1 of the ANN model activated. In addition, one or more neurons of the layer L2 may be activated. In some embodiments, for a given image (or a video) input, the objects may be stored in a hierarchical graph, as explained in greater detail in conjunction with FIG. 7.

Figure 7:
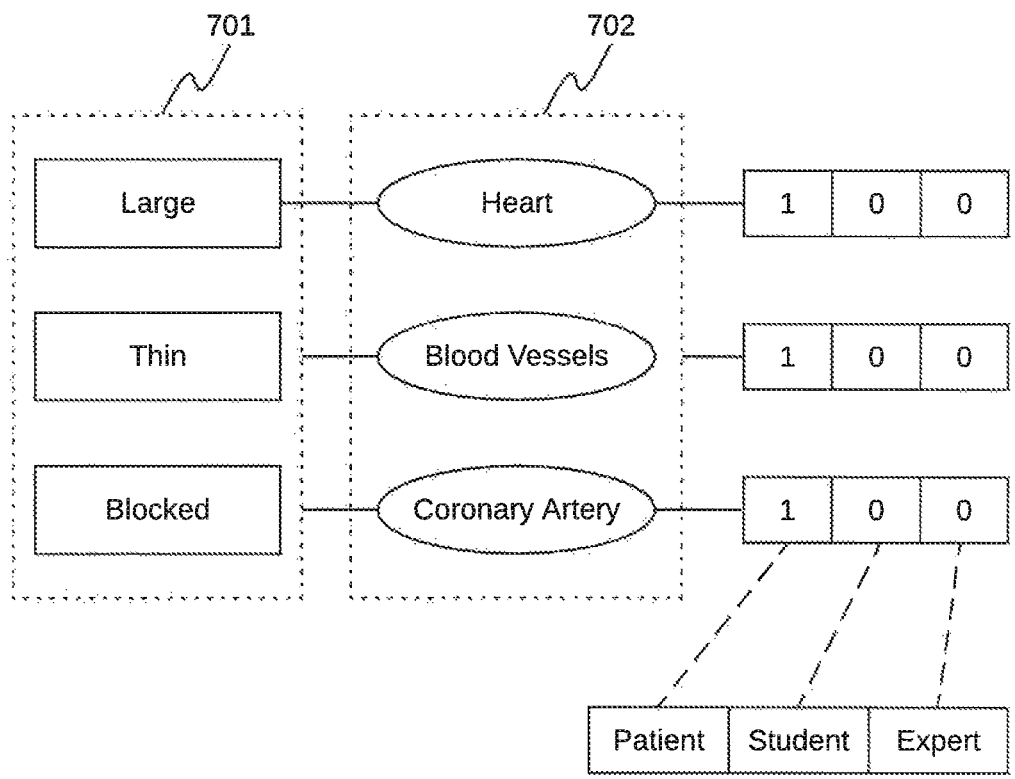
FIG. 7 is a hierarchical graph of objects and attributes, in accordance with some embodiments of the present disclosure.

Referring now to FIG. 7, a hierarchical graph 700 of objects and attributes is illustrated, in accordance with an embodiment. A column 701 of the hierarchical graph 700 includes attributes associated with respective objects in a column 702. Further, a column 702 includes respective vocabularies associated with the different user-groups. The vocabulary may be derived from the training dataset 207 provided by a domain expert or from the parsed words of captions of the image (or video). For example, for a user-group 'Patient', the associated object and attribute may include 'heart' and 'large', respectively. For example, for a user-group 'Student, the associated object and attribute may include 'blood-vessels' and 'thin, respectively. Further, for example, for a user-group 'Doctor, the associated object and attribute may include 'coronary-artery', and 'blocked', respectively. The explanation 209 of an output generated for the above image may be generated using the vocabularies, for each user-group. For example, for the user-group, 'Patient', the explanation 209 may be as below:

It is abnormal because the heart is large

Similarly, for the user-group 'Student', the explanation 209 may be as below:

It is abnormal because the blood-vessel is thin.

In some embodiments, possible captions and descriptors may be included in a Table (like Table 600) as sub-entries. For instance, in the above example, for an input image of a static X-ray of a heart with a coronary artery having a portion blocked, the object descriptors may include the heart, one or more blood vessels, the coronary artery, and the blocked portion of the coronary artery.

Figure 8:
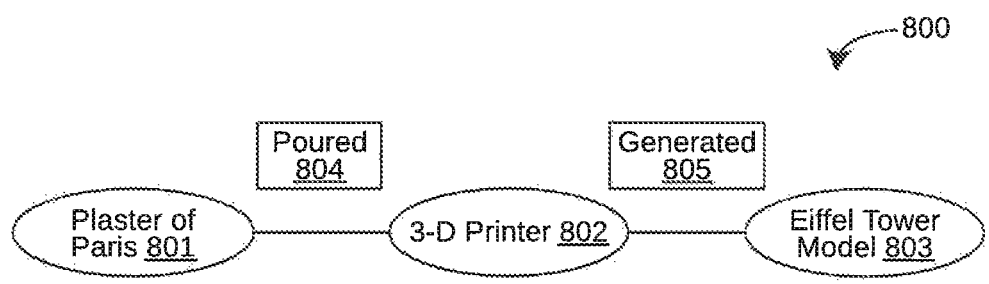
FIG. 8 is an exemplary video graph, in accordance with some embodiments of the present disclosure.

It may be noted that the explanations 209 may be generated in one or more languages, corresponding to each of the one or more user-groups. Referring now to FIG. 8, an exemplary video graph 800 is illustrated, in accordance with an example. The video graph 800 stores actions and interactions along with the objects. For example, the objects include 'Plaster of Paris' 801, '3-d Printer' 802, and 'Eiffel Tower Model' 803. The interactions include 'Poured' 804 and 'Generated' 805. The explanations for the video graph 800 may be generated in two languages, as shown below:

English:

Plaster of Paris poured to 3-d printer.

The 3-d printer generated Eiffel Tower Model.

French:

Plâtre de Paris coulé sur une imprimante 3D.

Le modelé de tour Eiffel géneré par.

Returning back to FIG. 5, at step 503, one or more training images may be received as input along with extracted features including the attributes. For example, the group feature identifying module 202 may receive the one or more training images. The group feature identifying module 202 may further receive the extracted features including the attributes from the feature generating module 201. In some embodiments, object specific data may be transferred from the feature generating module 201 to the group feature identifying module 202 for further processing.

At step 504, the attributes may be segregated by the group feature identifying module 202, to generate one or more user specific groups. The generated user specific groups may be organized into multiple levels hierarchically based on domain knowledge that the users of that group need to have to comprehend and use the explanation. Further, at step 504, a set of features that get into the vocabulary of explanation for a specific group of audience may be identified.

By way of an example, an image (or a video segment) and corresponding entity interested in the specific group may be determined. It may be understood that although the maximum depth of hierarchy in a hierarchy graph may indicate maximum possible groups (and explanations corresponding to the images making use of these vocabularies), it can be made less than that as well. For example, if there are 4 levels in a hierarchy, Level-1 can be in Category I, Level-2 and Level-3 can be in Category II, and Level-4 can be in Category III. Alternately, a hierarchy may fall in more than one category. These parameters may be configurable, and may be mapped to the set of users, for example, the set of users may be {patient, student, clinical expert}. For example, for an angiogram image input, an explanation for a 'clinical expert' user group may include "left coronary artery", while an explanation for a 'patient' user group, who is not familiar with medical terminologies, may include "Artery", although they refer to same image features for explanation. The classifier module 203 may be injected extensively with images of these features to generate signatures that may include desired features. The output of a LSTM model may be represented in a graphical form.

At step 505, a feature table may be generated by the group feature identifying module 202. The feature table may include attributes mapped to multiple levels of user groups. The feature table generated from the attributes of the image in hierarchical fashion (reflecting different user groups) may be stored in the data repository 206. It may be noted that these attributes may form the vocabulary for the explanation for different group of users. At step 506, the user-specific explanation module 204 may receive the feature table from the data repository 206, the image signatures from the classifier module 203, and group signatures 208 from a user.

At step 507, explanations 209 may be generated by the user-specific explanation module 204. The explanations 209 may be generated word by word in a sequence, based on the concatenated received data and the current word generated by the system. Further, at step 507, the classifier module 203 may be trained. An explanation model may be developed to generate the explanations 209 corresponding to the user groups. It may be understood that the explanation model may be trained to cater for more than one group of users. The user categories may be fed as external input to the model at the time of generating explanation 209 unique to the category. Essentially, the group signature 208 may be treated as extended feature for the selection of right vocabulary. By way of an example, the explanation model may include LSTM. The LSTM may be fed with the signatures of the image to be explained along with identity of the group to distinguish the explanations of different groups. It may be further understood that a group may be represented by a unique pattern and concatenated with penultimate layer output of the ANN model. The ANN model is further explained in detail, in conjunction with FIG. 9. Here, training also considers this auxiliary pattern to generate the explanation 209.

Figure 9:
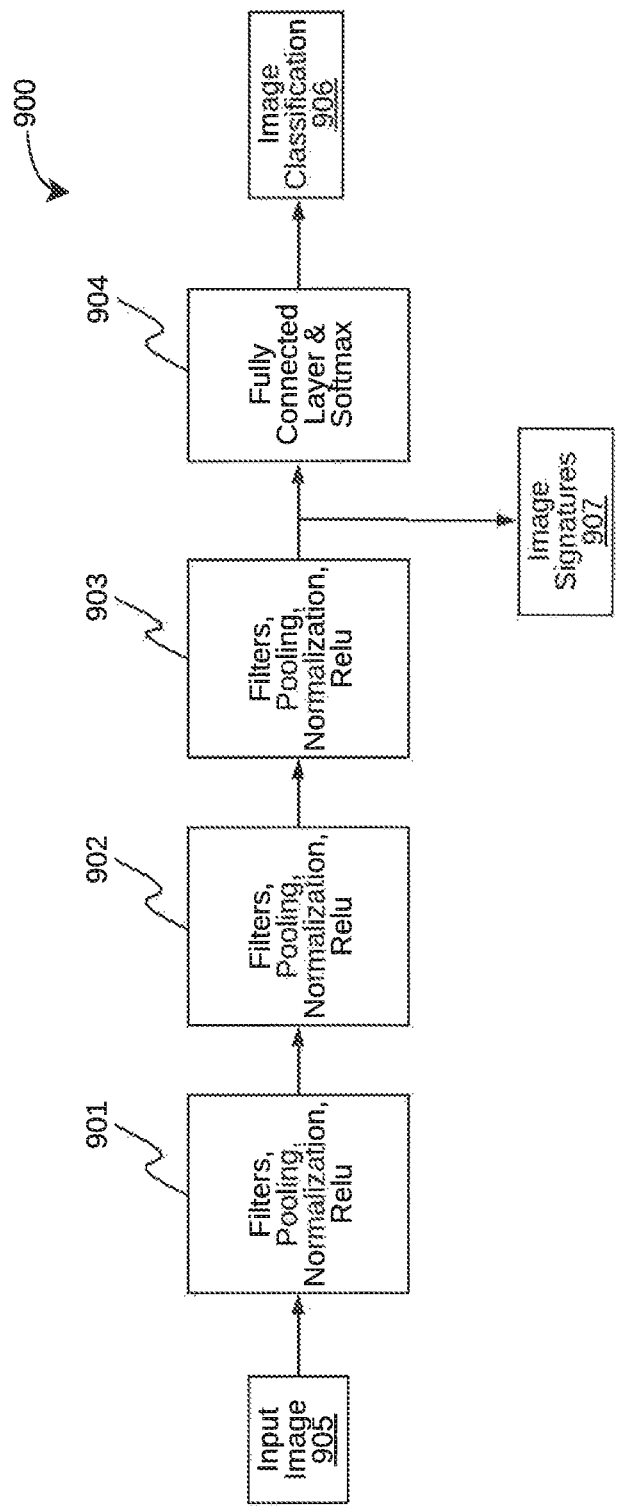
FIG. 9 is a functional block diagram of an ANN model for generating image signatures, in accordance with some embodiments of the present disclosure.

Referring now to FIG. 9, an ANN model 900 for generating image signatures is illustrated, in accordance with an embodiment. The ANN model 900 may include various layers 901-904. The ANN model 900 may be fed with an input image 905 for which the ANN model 900 may generate an output in form of image class 906. In some embodiments, image signatures 907 may be received after the penultimate layer 903. The training of the ANN model may consider an auxiliary pattern to generate the explanation. In some embodiments, activations of penultimate layer may form a fixed pattern for different classes. This output may be truncated so that only those features contributing for explanation for a specific category are retained. For example, a word like 'artery' may not be required and a word 'heart' may be sufficient in some cases.

Returning back to FIG. 5, at step 508, the generated explanations and corrections to be made to the explanations 209 may be received from the user. For example, the generated explanations 209 may be received by the vocabulary correction module 205 from the user-specific explanation module 204. At step 509, fine-tuning parameters may be sent by the vocabulary correction module 205 to the user-specific explanation module 204 for updating the generated explanations 209. It may be noted that the corrections to the explanations 209 may happen during a pilot period, through the user interaction. In some embodiments, if the user agrees to the explanation 209, a credit gets incremented by an amount equal to the number of correct words for the class. On the other hand, if the word of a different class is found in the explanation 209 (i.e. the user disagrees), the credit may be decremented, for example, by indicating a heavy penalty. If the user finds some explanation 209 is not matching with the input entity, the entity may be marked through user interface (UI). Similarly, appearance of additional words may be indicated over the UI. These words may then be mapped to the neurons of the ANN model using the feature, for example, Table 600. A discrepancy in the activation may be noted. To obtain the right choice of words, weights of the ANN model may be tuned to generate required target activations. A current activation may be mapped to the target activation through a non-linear transformation. In an embodiment, a Multilayer Perceptron may be used. Thereafter, the classifier model weights may be restored back.

At step 510, an input image and image signature corresponding to the input image may be received by the user-specific explanation module 204 from the classifier module 203, and the group signature 208 may be received from the user. At step 511, the explanations 209 may be generated by the user-specific explanation module 204. The explanations 209 may be generated word by word in a sequence based on the concatenated data obtained by combining the input image, the image signature, and the group signature 208. Further, at step 511, selective explanation 209 may be generated for a given image or video when the system is deployed. A right signature of the user-group may be applied to get the explanation 209 applicable to the specific class of user. This ensures authenticity to get the right explanation. In some embodiments, a password, for example, in form of an auxiliary pattern, may be provided to a specific user group. In some embodiments, the explanations 209 may be personalized to a specific user using his/her choice of words. In case the password is not matching, the explanation 209 may contain random words. The generated explanations 209 may be sent by the user-specific explanation module 204 to the vocabulary correction module 205. The vocabulary correction module 205 may receive the explanation 209 to look for the correctness of the words based on its relevance or fitness for the class. Thereafter, the user-specific explanation module 204 may receive the fine-tuning parameters from the vocabulary correction module 205. Accordingly, the relevance of different words in the explanation 209 may be received by the user-specific explanation module 204.

At step 512, the explanations 209 may be updated by the user-specific explanation module 204 based on the received fine-tuning parameters. The fine-tuning parameters may be in the form of varied probabilities for different words (that may indicate new words to be included or existing words to be excluded from a class vocabulary). The fine-tuning parameters may be provided to the explanation model which in turn may update the fine-tuning parameters in the vocabularies in the user-specific explanation module 204.

At step 513, the explanations 209 may be rendered by the user-specific explanation module 204 to the user. The explanation model may render a reason behind the classification based on the user class. The user class may be specified as password or signature unique to the group or the person. In some embodiments, the explanation 209 may be in the form of comprehendible text. In some embodiments, the explanation 209 may include simple figures.

Use Case 1:

For example, a hospital uses a decision support system to provide second opinion on the presence or absence of breast cancer from a Computed Tomography (CT) image, where the system provides detailed report of findings and the impression adequate for a radiologist to accept. However, the report may be comprehensive, but not detailed enough for a student of radiology to pursue as case study. Further, the report may not be in plain English to be understood by the patient. The hospital may implement the application as provided by the proposed invention which may provide distinct reports of the same information about required details, based on the needs of the user.

Use Case 2:

For example, organizers of a football match may use a robot powered by Artificial Intelligence (AI) to provide live commentary of the match. The commentary may be in English and subsequently translated to other languages with a delay of a few seconds. However, the delay and the quality of translation may not be acceptable to the audience. In such a scenario, the organizers may implement the application using the proposed invention which may be able to generate sentences (commentary) without delay and in multiple languages, making use of vocabularies and training models of multiple languages.

As will be also appreciated, the above described techniques may take the form of computer or controller implemented processes and apparatuses for practicing those processes. The disclosure can also be embodied in the form of computer program code containing instructions embodied in tangible media, such as floppy diskettes, solid state drives, CD-ROMs, hard drives, or any other computer-readable storage medium, wherein, when the computer program code is loaded into and executed by a computer or controller, the computer becomes an apparatus for practicing the invention. The disclosure may also be embodied in the form of computer program code or signal, for example, whether stored in a storage medium, loaded into and/or executed by a computer or controller, or transmitted over some transmission medium, such as over electrical wiring or cabling, through fiber optics, or via electromagnetic radiation, wherein, when the computer program code is loaded into and executed by a computer, the computer becomes an apparatus for practicing the invention. When implemented on a general-purpose microprocessor, the computer program code segments configure the microprocessor to create specific logic circuits.

Figure 10:
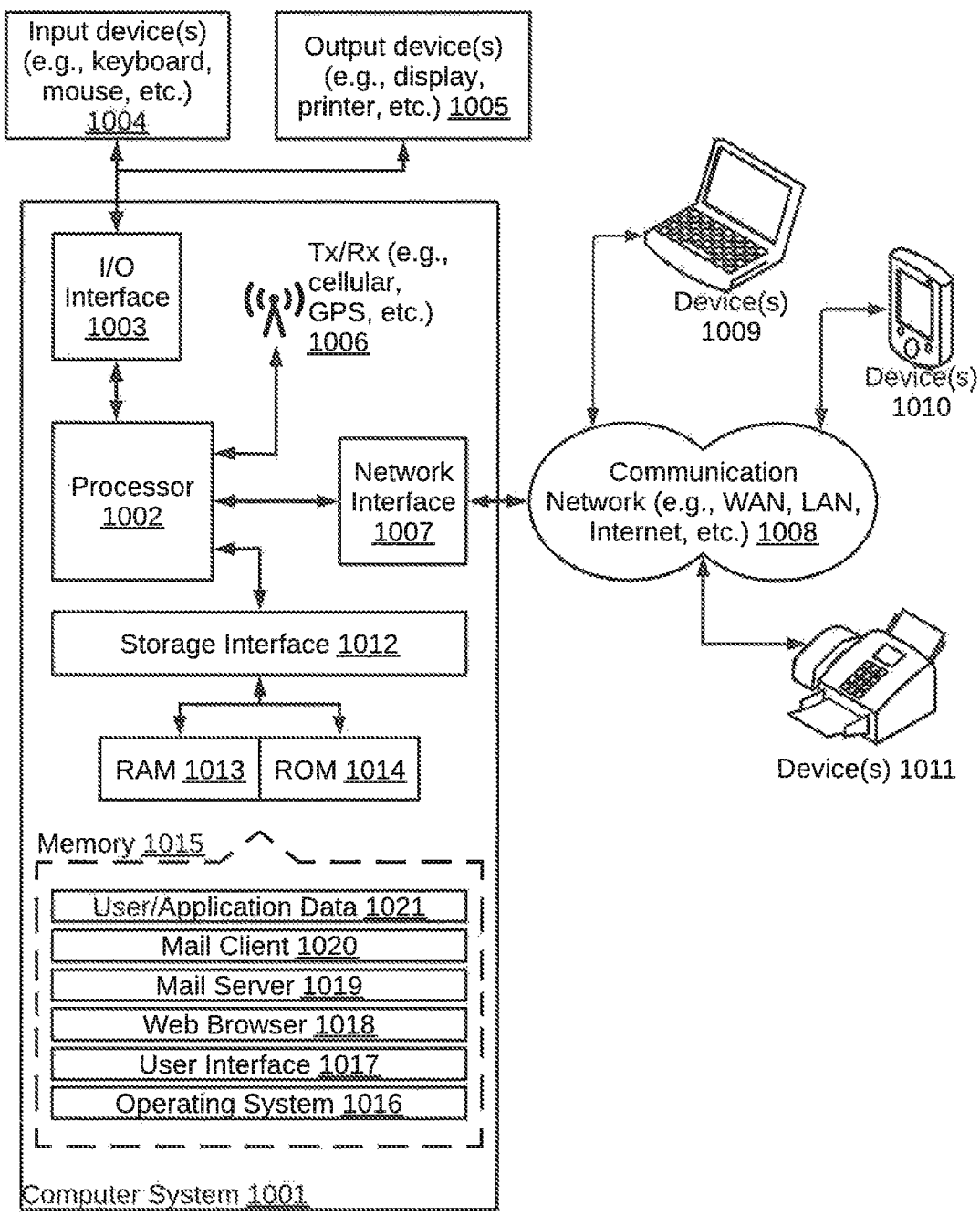
FIG. 10 is a block diagram of an exemplary computer system for implementing embodiments consistent with the present disclosure.

The disclosed methods and systems may be implemented on a conventional or a general-purpose computer system, such as a personal computer (PC) or server computer. Referring now to FIG. 10, a block diagram of an exemplary computer system 1001 for implementing embodiments consistent with the present disclosure is illustrated. Variations of computer system 1001 may be used for implementing system 100 for providing user-specific explanations for an output generated by an ANN. Computer system 1001 may include a central processing unit ("CPU" or "processor") 1002. Processor 1002 may include at least one data processor for executing program components for executing user-generated or system-generated requests. A user may include a person, a person using a device such as those included in this disclosure, or such a device itself. The processor 1002 may include specialized processing units such as integrated system (bus) controllers, memory management control units, floating point units, graphics processing units, digital signal processing units, etc. The processor 1002 may include a microprocessor, such as AMD® ATHLON®, DURON® OR OPTERON®, ARM's application, embedded or secure processors, IBM® POWERPC®, INTEL® CORE® processor, ITANIUM® processor, XEON® processor, CEL- ERON® processor or other line of processors, etc. The processor 1002 may be implemented using mainframe, distributed processor, multi-core, parallel, grid, or other architectures. Some embodiments may utilize embedded technologies like application-specific integrated circuits (ASICs), digital signal processors (DSPs), Field Programmable Gate Arrays (FPGAs), etc.

Processor 1002 may be disposed in communication with one or more input/output (I/O) devices via I/O interface 1003. The I/O interface 1003 may employ communication protocols/methods such as, without limitation, audio, analog, digital, monoaural, RCA, stereo, IEEE-1394, near field communication (NFC), FireWire, Camera Link®, GigE, serial bus, universal serial bus (USB), infrared, PS/2, BNC, coaxial, component, composite, digital visual interface (DVI), high-definition multimedia interface (HDMI), radio frequency (RF) antennas, S-Video, video graphics array (VGA), IEEE 802.n/b/g/n/x, Bluetooth, cellular (e.g., code-division multiple access (CDMA), high-speed packet access (HSPA+), global system for mobile communications (GSM), long-term evolution (LTE), WiMAX, or the like), etc.

Using the I/O interface 1003, the computer system 1001 may communicate with one or more I/O devices. For example, the input device 1004 may be an antenna, keyboard, mouse, joystick, (infrared) remote control, camera, card reader, fax machine, dongle, biometric reader, microphone, touch screen, touchpad, trackball, sensor (e.g., accelerometer, light sensor, GPS, altimeter, gyroscope, proximity sensor, or the like), stylus, scanner, storage device, transceiver, video device/source, visors, etc. Output device 1005 may be a printer, fax machine, video display (e.g., cathode ray tube (CRT), liquid crystal display (LCD), light-emitting diode (LED), plasma, or the like), audio speaker, etc. In some embodiments, a transceiver 1006 may be disposed in connection with the processor 1002. The transceiver 1006 may facilitate various types of wireless transmission or reception. For example, the transceiver 1006 may include an antenna operatively connected to a transceiver chip (e.g., TEXAS INSTRUMENTS® WILINK WL1286®, BROADCOM® BCM4550IUB8®, INFINEON TECHNOLOGIES® X-GOLD 618-PMB9800® transceiver, or the like), providing IEEE 802.11a/b/g/n, Bluetooth, FM, global positioning system (GPS), 2G/3G HSDPA/HSUPA communications, etc.

In some embodiments, the processor 1002 may be disposed in communication with a communication network 1008 via a network interface 1007. The network interface 1007 may communicate with the communication network 1008. The network interface 1007 may employ connection protocols including, without limitation, direct connect, Ethernet (e.g., twisted pair 10/100/1000 Base T), transmission control protocol/internet protocol (TCP/IP), token ring, IEEE 802.11a/b/g/n/x, etc. The communication network 1008 may include, without limitation, a direct interconnection, local area network (LAN), wide area network (WAN), wireless network (e.g., using Wireless Application Protocol), the Internet, etc. Using the network interface 1007 and the communication network 1008, the computer system 1001 may communicate with devices 1009, 1010, and 1011. These devices 1009, 1010, and 1011 may include, without limitation, personal computer(s), server(s), fax machines, printers, scanners, various mobile devices such as cellular telephones, smartphones (e.g., APPLE® IPHONE®, BLACKBERRY® smartphone, ANDROID® based phones, etc.), tablet computers, eBook readers (AMAZON® KINDLE®, NOOK® etc.), laptop computers, notebooks, gaming consoles (MICROSOFT® XBOX®, NINTENDO® DS®, SONY® PLAYSTATION®, etc.), or the like. In some embodiments, the computer system 1001 may itself embody one or more of these devices 1009, 1010, and 1011.

In some embodiments, the processor 1002 may be disposed in communication with one or more memory devices 1015 (e.g., RAM 1013, ROM 1014, etc.) via a storage interface 1012. The storage interface 1012 may connect to memory devices 1015 including, without limitation, memory drives, removable disc drives, etc., employing connection protocols such as serial advanced technology attachment (SATA), integrated drive electronics (IDE), IEEE-1394, universal serial bus (USB), fiber channel, small computer systems interface (SCSI), STD Bus, RS-232, RS-422, RS-485, I2C, SPI, Microwire, 1-Wire, IEEE 1284, Intel® QuickPathInterconnect, InfiniBand, PCIe, etc. The memory drives may further include a drum, magnetic disc drive, magneto-optical drive, optical drive, redundant array of independent discs (RAID), solid-state memory devices, solid-state drives, etc.

The memory devices 1015 may store a collection of program or database components, including, without limitation, an operating system 1016, user interface application 1017, web browser 1018, mail server 1019, mail client 1020, user/application data 1021 (e.g., any data variables or data records discussed in this disclosure), etc. The operating system 1016 may facilitate resource management and operation of the computer system 1001. Examples of operating systems 1016 include, without limitation, APPLE® MACINTOSH® OS X, UNIX, Unix-like system distributions (e.g., Berkeley Software Distribution (BSD), FreeBSD, NetBSD, OpenBSD, etc.), Linux distributions (e.g., RED HAT®, UBUNTU®, KUBUNTU®, etc.), IBM® OS/2, MICROSOFT® WINDOWS® (XP®, Vista®/7/8, etc.), APPLE® IOS®, GOOGLE® ANDROID®, BLACKBERRY® OS, or the like. User interface 1017 may facilitate display, execution, interaction, manipulation, or operation of program components through textual or graphical facilities. For example, user interfaces 1017 may provide computer interaction interface elements on a display system operatively connected to the computer system 1001, such as cursors, icons, check boxes, menus, scrollers, windows, widgets, etc. Graphical user interfaces (GUIs) may be employed, including, without limitation, APPLE® MACINTOSH® operating systems' AQUA® platform, IBM® OS/2®, MICROSOFT® WINDOWS® (e.g., AERO®, METRO®, etc.), UNIX X-WINDOWS, web interface libraries (e.g., ACTIVEX®, JAVA®, JAVASCRIPT®, AJAX®, HTML, ADOBE® FLASH®, etc.), or the like.

In some embodiments, the computer system 1001 may implement a web browser 1018 stored program component. The web browser 1018 may be a hypertext viewing application, such as MICROSOFT® INTERNET EXPLORER®, GOOGLE® CHROME®, MOZILLA® FIREFOX®, APPLE® SAFARI®, etc. Secure web browsing may be provided using HTTPS (secure hypertext transport protocol), secure sockets layer (SSL), Transport Layer Security (TLS), etc. Web browsers may utilize facilities such as AJAX®, DHTML, ADOBE® FLASH®, JAVASCRIPT®, JAVA®, application programming interfaces (APIs), etc. In some embodiments, the computer system 1001 may implement a mail server 1019 stored program component. The mail server 1019 may be an Internet mail server such as MICROSOFT® EXCHANGE®, or the like. The mail server 1019 may utilize facilities such as ASP, ActiveX, ANSI C++/C #, MICROSOFT .NET® CGI scripts, JAVA®, JAVASCRIPT®, PERL®, PHP®, PYTHON®, WebObjects, etc. The mail server 1019 may utilize communication protocols such as internet message access protocol (IMAP), messaging application programming interface (MAPI), MICROSOFT® EXCHANGE®, post office protocol (POP), simple mail transfer protocol (SMTP), or the like. In some embodiments, the computer system 1001 may implement a mail client 1020 stored program component. The mail client 1020 may be a mail viewing application, such as APPLE MAIL®, MICROSOFT ENTOURAGE®, MICROSOFT OUTLOOK®, MOZILLA THUNDERBIRD®, etc.

In some embodiments, computer system 1001 may store user/application data 1021, such as the data, variables, records, etc. (e.g., activated neurons data, Characteristic Feature Directives (CFDs) data, differentiating neurons data, missing features data, new training data, and so forth) as described in this disclosure. Such databases may be implemented as fault-tolerant, relational, scalable, secure databases such as ORACLE® OR SYBASE®. Alternatively, such databases may be implemented using standardized data structures, such as an array, hash, linked list, struct, structured text file (e.g., XML), table, or as object-oriented databases (e.g., using OBJECTSTORE®, POET®, ZOPE®, etc.). Such databases may be consolidated or distributed, sometimes among the various computer systems discussed above in this disclosure. It is to be understood that the structure and operation of the any computer or database component may be combined, consolidated, or distributed in any working combination.

As will be appreciated by those skilled in the art, the techniques described in the various embodiments discussed above are not routine, or conventional, or well understood in the art. The techniques discussed above provide for providing user-specific explanations for an output generated by an ANN model by extracting relevant features from the training image, segregating attributes to generate one or more user specific groups, generating a feature table, generating explanations word by word in a sequence based on the concatenated received data and the current word generated by the system, and updating the explanations based on the received fine-tuning parameters.

In particular, the techniques discussed above provide selective explanations based on the domain knowledge level of a user (i.e. user-specific explanations), thereby allowing the user to use the proposed system efficiently and for the purpose intended. Further, the techniques can be extended to provide language specific explanations or provide language translations, which would allow increased adaptability of the proposed techniques. By building a vocabulary along with model development, the techniques provide for a time-efficient and energy-efficient solution. The techniques take into consideration activations of the neurons responsible for different attributes, so as to provide user-specific explanations. Further, attributes provided from the users (domain experts) are based on an overall or holistic perspective, rather than specific unmistakable signatures found in certain neurons of the model. For example, considering a scenario where a cardiac image is fed to a classifier model (AI model), and a neuron representing blockage in an artery is activated. Now, if an end-user is a cardiologist (i.e. domain expert), the explanation may be "88% blockage" based on the degree of activation of this neuron and other neurons representing blockage. On the other hand, if the user is a patient, the explanation may be "issue in arteries" based on whether the neurons corresponding to malfunctioning arteries are activated.

Further, the techniques described above may be employed in any kind of ANN including, but not limited to, deep neural network (DNN) such as recurrent neural network (RNN), convolutional neural network (CNN), or the like. Moreover, the techniques may be easily deployed in any cloud-based servers for access and use as an 'application as a service' by any computing device including mobile device. For example, the ANN improvement engine may be implemented on a cloud-based server and used for improving performance of various ANN based mobile device applications.

The specification has described method and system for providing user-specific explanations for an output generated by an ANN model. The illustrated steps are set out to explain the exemplary embodiments shown, and it should be anticipated that ongoing technological development will change the manner in which particular functions are performed. These examples are presented herein for purposes of illustration, and not limitation. Further, the boundaries of the functional building blocks have been arbitrarily defined herein for the convenience of the description. Alternative boundaries can be defined so long as the specified functions and relationships thereof are appropriately performed. Alternatives (including equivalents, extensions, variations, deviations, etc., of those described herein) will be apparent to persons skilled in the relevant art(s) based on the teachings contained herein. Such alternatives fall within the scope and spirit of the disclosed embodiments.

Furthermore, one or more computer-readable storage media may be utilized in implementing embodiments consistent with the present disclosure. A computer-readable storage medium refers to any type of physical memory on which information or data readable by a processor may be stored. Thus, a computer-readable storage medium may store instructions for execution by one or more processors, including instructions for causing the processor(s) to perform steps or stages consistent with the embodiments described herein. The term "computer-readable medium" should be understood to include tangible items and exclude carrier waves and transient signals, i.e., be non-transitory. Examples include random access memory (RAM), read-only memory (ROM); volatile memory, nonvolatile memory, hard drives, CD ROMs, DVDs, flash drives, disks, and any other known physical storage media.

It is intended that the disclosure and examples be considered as exemplary only, with a true scope and spirit of disclosed embodiments being indicated by the following claim.

What is claimed is:

1. A method of providing user-specific explanations for an output generated by an Artificial Neural Network (ANN) model, the method comprising:
   receiving, by a vocabulary and explanation generating device, a training dataset;
   identifying, by the vocabulary and explanation generating device, one or more relevant features from the training dataset, wherein the one or more relevant features are identified from a plurality of features associated with the training dataset, and wherein each of the plurality of features correspond to a neuron activated in the ANN model for generating an output for the training dataset, wherein identifying further comprises selecting the one or more relevant features from the plurality of features associated with the training dataset based on a predetermined threshold level of activation of the neuron corresponding to the each of the plurality of features;
   distributing, by the vocabulary and explanation generating device, the one or more relevant features into a plurality of groups, wherein the plurality of groups correspond to a plurality of levels of domain knowledge of users; and generating, by the vocabulary and explanation generating device, a plurality of vocabularies of explanations for an output generated by the ANN model for the training dataset corresponding to the plurality of groups, using the one or more relevant features.

2. The method of claim 1 further comprising:
receiving a test dataset;
receiving a target group signature corresponding to a target group from the plurality of groups; and
selecting a vocabulary of explanation for the output generated by the ANN model for the test dataset from the plurality of vocabularies of explanations, based on the target group signature.

3. The method of claim 2, wherein the training dataset and the test dataset comprises at least one of an image file and a video file.

4. The method of claim 3, wherein generating the plurality of vocabularies of explanations comprise receiving one or more captions corresponding to each of the one or more relevant features, wherein the one or more captions are generated using Common Objects in Context (COCO), and wherein the one or more attributes associated with each of the one or more relevant features are generated from the one or more captions using Natural Language Processing (NLP).

5. The method of claim 1, wherein the one or more relevant features comprise at least one of one or more objects within the training dataset, an interaction between two or more objects within the training dataset, an action associated with an object, or one or more attributes associated with each of the one or more objects, wherein the one or more attributes comprise at least one of a color of the object, a shape of the object, a size of the object, a position of the object, or an interaction of the object with other objects and surroundings.

6. The method of claim 1 further comprising generating a plurality of explanations for the output generated by the ANN model for the training dataset corresponding to the plurality of groups, using the plurality of vocabularies of explanations, wherein the plurality of explanations are generated from the plurality of vocabularies of explanations using Long Short Term Memory (LSTM) model.

7. The method of claim 6 further comprising:
receiving, from a user, a correction to an explanation of the plurality of explanations, wherein the correction to the explanation is based on at least one of:
determining by the user that a word in the explanation corresponding to a group of the plurality of groups is from a vocabulary of explanation corresponding to the group, and
determining by the user that a word in the explanation corresponding to a group is from a correct vocabulary of explanation corresponding to the group.

8. The method of claim 1, wherein generating the plurality of vocabularies of explanations comprises:
receiving a dataset signature corresponding to the training dataset from the ANN model;
receiving a group signature corresponding to each of the plurality of groups;
receiving a feature table, wherein the feature table comprises connecting words of a language; and
generating a vocabulary for a group of the plurality of groups based on the dataset signature, the group signature, and the feature table.

9. The method of claim 8, wherein generating the plurality of vocabularies of explanations further comprises feeding the one or more relevant features of the training dataset at an output of a penultimate layer of the ANN model.

10. The method of claim 1 further comprising:
upon distributing the one or more relevant features into a plurality of groups, arranging and storing the one or more relevant features in form of a hierarchical graph, wherein the hierarchical graph represents the plurality of levels of domain knowledge of the users.

11. A system for providing user-specific explanations for an output generated by an ANN model, the system comprising:
a vocabulary and explanation generating device comprising at least one processor and a computer-readable medium storing instructions that, when executed by the at least one processor, cause the at least one processor to perform operations comprising:
receiving a training dataset;
identifying one or more relevant features from the training dataset, wherein the one or more relevant features are identified from a plurality of features associated with the training dataset, and wherein each of the plurality of features correspond to a neuron activated in the ANN model for generating an output for the training dataset, wherein identifying further selecting the one or more relevant features from the plurality of features associated with the training dataset based on a predetermined threshold level of activation of the neuron corresponding to the each of the plurality of features;
distributing the one or more relevant features into a plurality of groups, wherein the plurality of groups correspond to a plurality of levels of domain knowledge of users; and
generating a plurality of vocabularies of explanations for an output generated by the ANN model for the training dataset corresponding to the plurality of groups, using the one or more relevant features.

12. The system of claim 11, wherein the operations further comprise:
receiving a test dataset;
receiving a target group signature corresponding to a target group from the plurality of groups; and
selecting a vocabulary of explanation for the output generated by the ANN model for the test dataset from the plurality of vocabularies of explanations, based on the target group signature.

13. The system of claim 11, wherein generating the plurality of vocabularies of explanations comprise:
receiving one or more captions corresponding to each of the one or more relevant features, wherein the one or more captions are generated using Common Objects in Context (COCO), and wherein one or more attributes associated with each of the one or more relevant features are generated from the one or more captions using Natural Language Processing (NLP);
receiving a dataset signature corresponding to the training dataset from the ANN model;
receiving a group signature corresponding to each of the plurality of groups;
receiving a feature table, wherein the feature table comprises connecting words of a language; and
generating a vocabulary for a group of the plurality of groups based on the dataset signature, the group signature, and the feature table.

14. The system of claim 11, wherein the operations further comprise generating a plurality of explanations for the output generated by the ANN model for the training dataset corresponding to the plurality of groups, using the plurality of vocabularies of explanations, wherein the plurality of explanations are generated from the plurality of vocabularies of explanations using Long Short Term Memory (LSTM) model.

15. The system of claim 14, wherein the operations further comprise:
receiving, from a user, a correction to an explanation of the plurality of explanations, wherein the correction to the explanation is based on at least one of:
determining by the user that a word in the explanation corresponding to a group of the plurality of groups is from a vocabulary of explanation corresponding to the group, and
determining by the user that a word in the explanation corresponding to a group is from a correct vocabulary of explanation corresponding to the group.

16. The system of claim 11, wherein the operations further comprise:
upon distributing the one or more relevant features into a plurality of groups, arranging and storing the one or more relevant features in form of a hierarchical graph, wherein the hierarchical graph represents the plurality of levels of domain knowledge of the users.

17. A non-transitory computer-readable medium storing computer-executable instructions for providing user-specific explanations for an output generated by an Artificial Neural Network (ANN) model, the computer-executable instructions, when executed by at least one processor, cause the at least one processor to perform operations comprising:
receiving a training dataset;
identifying one or more relevant features from the training dataset, wherein the one or more relevant features are identified from a plurality of features associated with the training dataset, and wherein each of the plurality of features correspond to a neuron activated in the ANN model for generating an output for the training dataset, wherein identifying further comprising selecting the one or more relevant features from the plurality of features associated with the training dataset based on a predetermined threshold level of activation of the neuron corresponding to the each of the plurality of features;
distributing the one or more relevant features into a plurality of groups, wherein the plurality of groups corresponds to a plurality of levels of domain knowledge of users; and
generating a plurality of vocabularies of explanations for an output generated by an ANN model for the training dataset corresponding to the plurality of groups, using the one or more relevant features.

\* \* \* \* \*